(12) United States Patent
Degraff et al.

(10) Patent No.: US 11,808,646 B2
(45) Date of Patent: Nov. 7, 2023

(54) CARBON NANOTUBE SENSORS, ARTICLES, AND METHODS

(71) Applicants: THE FLORIDA STATE UNIVERSITY RESEARCH FOUNDATION, INC., Tallahassee, FL (US); INSTITUT NATIONAL DES SCIENCES APPLIQUEES DE LYON, Villeurbanne (FR)

(72) Inventors: Joshua H. Degraff, Tallahassee, FL (US); Pierre-Jean Cottinet, Villeurbanne (FR); Zhiyong Liang, Tallahassee, FL (US)

(73) Assignees: The Florida State University Research Foundation, Inc., Tallahassee, FL (US); Institut National Des Sciences Appliquees De Lyon, Villeurbanne (FR)

( * ) Notice: Subject to any disclaimer, the term of this patent is extended or adjusted under 35 U.S.C. 154(b) by 399 days.

(21) Appl. No.: 17/053,147

(22) PCT Filed: May 29, 2019

(86) PCT No.: PCT/US2019/034339
§ 371 (c)(1),
(2) Date: Nov. 5, 2020

(87) PCT Pub. No.: WO2019/232013
PCT Pub. Date: Dec. 5, 2019

(65) Prior Publication Data
US 2021/0239548 A1 Aug. 5, 2021

Related U.S. Application Data

(60) Provisional application No. 62/677,310, filed on May 29, 2018.

(51) Int. Cl.
*G01L 1/00* (2006.01)
*G01L 1/22* (2006.01)
(Continued)

(52) U.S. Cl.
CPC .......... *G01L 1/2293* (2013.01); *A61B 5/1114* (2013.01); *A61B 5/6806* (2013.01);
(Continued)

(58) Field of Classification Search
CPC ....... G01L 1/2293; G01L 1/18; G01L 1/2262; A61B 5/1114; A61B 5/6806;
(Continued)

(56) References Cited

U.S. PATENT DOCUMENTS 7,318,908 B1 * 1/2008 Dai ...................... G01N 33/551
422/50
8,020,456 B2 9/2011 Liu et al.
(Continued)

FOREIGN PATENT DOCUMENTS

JP 2016127898 A 7/2016

OTHER PUBLICATIONS

Degraff et al., "Printable low-cost and flexible carbon nanotube buckypaper motion sensors", Materials & Design, 133: 47-53 (Jul. 25, 2017).

*Primary Examiner* — Max H Noori
(74) *Attorney, Agent, or Firm* — Eversheds Sutherland (US) LLP

(57) ABSTRACT

Sensors that include carbon nanotubes, and articles that include the sensors. The sensors may include a buckypaper. The sensors may be flexible. Methods of making sensors, which may include printing an electrode on a substrate. The printing of an electrode may be achieved with an inkjet printer.

21 Claims, 5 Drawing Sheets

(51) Int. Cl.
  *A61B 5/11* (2006.01)
  *A61B 5/00* (2006.01)
  *G01L 1/18* (2006.01)
(52) U.S. Cl.
  CPC .............. *G01L 1/18* (2013.01); *G01L 1/2262* (2013.01); *A61B 2562/0261* (2013.01); *A61B 2562/0285* (2013.01); *A61B 2562/125* (2013.01)
(58) Field of Classification Search
  CPC .... A61B 2562/0261; A61B 2562/0285; A61B 2562/125
  See application file for complete search history.

(56) References Cited

U.S. PATENT DOCUMENTS

| | | | |
|---|---|---|---|
| 8,784,603 B2 | 7/2014 | Liang et al. | |
| 10,391,703 B2 | 8/2019 | Bao et al. | |
| 10,586,629 B2 | 3/2020 | Liang et al. | |
| 2006/0076790 A1* | 4/2006 | Maslov | B25J 7/00 294/86.4 |
| 2007/0222472 A1 | 9/2007 | Raravikar et al. | |
| 2010/0012927 A1* | 1/2010 | Jaiprakash | H01L 21/76838 257/E51.024 |
| 2011/0147715 A1* | 6/2011 | Rogers | H10K 71/20 257/E29.245 |
| 2011/0210282 A1* | 9/2011 | Foley | B82Y 25/00 252/301.36 |
| 2011/0262729 A1 | 10/2011 | Chen et al. | |
| 2014/0154847 A1* | 6/2014 | Kastalsky | H01L 29/45 438/167 |
| 2015/0276649 A1* | 10/2015 | Farrow | G01N 33/48728 205/792 |
| 2016/0139069 A1* | 5/2016 | Wang | B01L 3/50273 438/49 |
| 2016/0153762 A1* | 6/2016 | Li | G01L 1/18 73/774 |
| 2019/0092640 A1 | 3/2019 | Zeng et al. | |

* cited by examiner

CARBON NANOTUBE SENSORS, ARTICLES, AND METHODS

CROSS-REFERENCE TO RELATED APPLICATIONS

This application claims priority to U.S. Patent Application No. 62/677,310, filed May 29, 2018, which is incorporated herein by reference.

STATEMENT REGARDING FEDERALLY SPONSORED RESEARCH OR DEVELOPMENT

This invention was made with government support under Contract No. SNM 1344672 awarded by the National Science Foundation. The government has certain rights in this invention.

BACKGROUND

Wearable technology has the potential to improve and increase the ways biomechanical data are collected. Subtle micro-strains (µm/m) have been difficult to detect, however, especially via imaging technology. Integrating low-profile sensors into wearable materials, such as fabrics, has the potential to provide real-time biomechanical information. Smart clothing, for example, could be used to monitor and/or provide feedback regarding subtle and/or noticeable body movements, thereby leading to improved methods of rehabilitation, training, and/or monitoring.

Currently, flexible sensors commonly include thin polymer substrates, because the thinness of the substrates generally promotes flexibility. Nanocomposite sensors have been prepared by dispersing relatively small amounts of carbon nanotubes (CNTs) into polymers, such as polyimide, polyethylene terephthalate (PET), and epoxy. Flexible CNT/polymer nanocomposites have displayed piezoresistive responses to small strains, and the CNTs themselves can have a high (1) tensile strength (e.g., ~100 GPa), (2) Young's modulus (e.g., ~1 TPa), (3) electrical conductivity (e.g., $10^6$-$10^7$ S/m), and/or (4) aspect ratio (>$10^6$), which may be attractive features in the development of multifunctional materials (see, e.g., Bautista-Quijano, J. R. et al. Sensors and Actuators A: Physical, 2010. 159(2): p. 135-140; Alamusi, N. et al. Sensors, 2011. 11(11): p. 10691; and Cai, L., et al. Scientific Reports, 2013. 3: p. 3048). The CNT/polymer composites' electrical conductivity also has been demonstrated to obey, at least in most instances, a well-established, percolation-like power law (see, e.g., Coleman, J. N. et al. Physical Review B, 1998, 58(12), R7492-R7495).

Buckypapers are carbon nanotube networks that typically exhibit higher sensitivities to local distributions of stress. Also, buckypapers that include multi-wall carbon nanotubes can have a well-distributed, yet random structure that can be exploited to sense stress in multiple directions (see, e.g., Rein, M. D. et al. Composites Science and Technology, 2011, 71(3), 373-381). Recently, strain sensors have been reported that include a buckypaper of aligned multi-wall carbon nanotubes that has been infiltrated with a polyurethane resin (Suzuki, K. et al. ACS Sensors, 2016, 1(6), 817-825). The buckypaper/polyurethane sensors have a gauge factor (GF) of 10.5, which is relatively large. Gauge factor is a metric for measuring sensor sensitivity, because it expresses the change in a sensor's electrical resistance with respect to the induced strain.

Recent advances in printing technology and patterning techniques have led to progress in printing low-profile electronics on flexible plastics. Although cheaper metallic-printed sensors have been made from relatively simple fabrication processes, semiconductor strain gauges have outperformed the cheaper metallic-printed sensors due at least in part to the higher sensitivities of the semiconductor strain gauges. Semiconductor strain gauges, however, typically are fragile, brittle, expensive, temperature-dependent, and/or possess a limited strain range.

The fabrication of strain gauges, including stretchable strain gauges, having a high sensitivity, optical transparency, durability, and/or stability remains a challenge.

There remains a need for sensors that are affordable, easy to manufacture, and/or easy to integrate into wearable materials, such as fabrics. There also remains a need for sensing devices that have a low profile, are flexible, provide quick, but consistent, responses with high sensitivity, and/or require minimal power.

BRIEF SUMMARY

Provided herein are embodiments of sensors, including sensors that may be made, at least in part, by printing one or more components. The sensors provided herein may include low profile strain sensors, which may include buckypapers. The sensors provided herein, in some embodiments, are more sensitive, to a surprising degree, than comparable sensors.

In one aspect, sensors are provided. In some embodiments, the sensors include a substrate having a first surface and a second surface; an electrode disposed on the first surface of the substrate, the electrode including a first contact and a second contact; and a buckypaper having (i) a first portion that contacts the first contact of the electrode, and (ii) a second portion that contacts the second contact of the electrode. The substrate may be flexible. The sensors also may include a laminating film. The laminating film may be disposed on at least a portion of (i) the first surface of the substrate, (ii) the second surface of the substrate, or (iii) a combination thereof.

In another aspect, articles are provided. In some embodiments, the articles include a sensor as described herein. An article may be a wearable article, such as clothing, an accessory, a medical device, etc.

In a further aspect, methods of forming a sensor are provided. In some embodiments, the methods include providing an electrode disposed on a substrate, wherein the electrode includes a first contact and a second contact; providing a buckypaper having a first portion and a second portion; and arranging the buckypaper such that the first portion of the buckypaper contacts the first contact of the electrode, and the second portion of the buckypaper contacts the second contact of the electrode to form the sensor. The providing of the electrode may include disposing an ink on the substrate to form the electrode, wherein the ink includes (i) a liquid and conductive metal particles, or (ii) a molten metal.

Additional aspects will be set forth in part in the description which follows, and in part will be obvious from the description, or may be learned by practice of the aspects described herein. The advantages described herein will be realized and attained by means of the elements and combinations particularly pointed out in the appended claims. It is to be understood that both the foregoing general description and the following detailed description are exemplary and explanatory only and are not restrictive.

DETAILED DESCRIPTION

Provided herein are methods of making sensors, and sensors, which may be flexible sensors. The sensors may include a buckypaper. The sensors provided herein, which may include strain sensors, may be sensitive and/or low-cost sensors. Embodiments of the sensors may be made by methods that take advantage of printed electronics and/or one or more properties of buckypapers (BPs) that include multi-wall carbon nanotubes (MWCNTs). The MWCNT BPs may have a low-profile (e.g., 7 µm), a relatively light weight (e.g., 5 g/m$^2$), and/or an ability to sense micro-strain.

In some embodiments, the sensors provided herein are made with relatively simple manufacturing methods, and can be sewn into fabrics or other materials.

The sensors described herein can be deployed in various applications, including structural wearable technology, structural health monitoring, etc.

In some embodiments, the sensors provided herein are flexible sensors. The flexible sensors may exhibit surprising improvement in response sensitivity compared to commercially available metallic strain gauges. For example, the flexible sensors provided herein may demonstrate at least a 700% improvement in response sensitivity compared to commercially available metallic strain gauges.

Sensors

Sensors, including strain sensors, are provided. In some embodiments, the sensors include a substrate having a first surface and a second surface; an electrode disposed on the first surface of the substrate, the electrode including a first contact and a second contact; and a buckypaper having (i) a first portion that contacts the first contact of the electrode, and (ii) a second portion that contacts the second contact of the electrode.

In some embodiments, the sensors include a laminating film. The laminating film may be disposed on at least a portion of (i) the first surface of the substrate, (ii) the second surface of the substrate, or (iii) the first surface and the second surface of the substrate.

Figure 1:
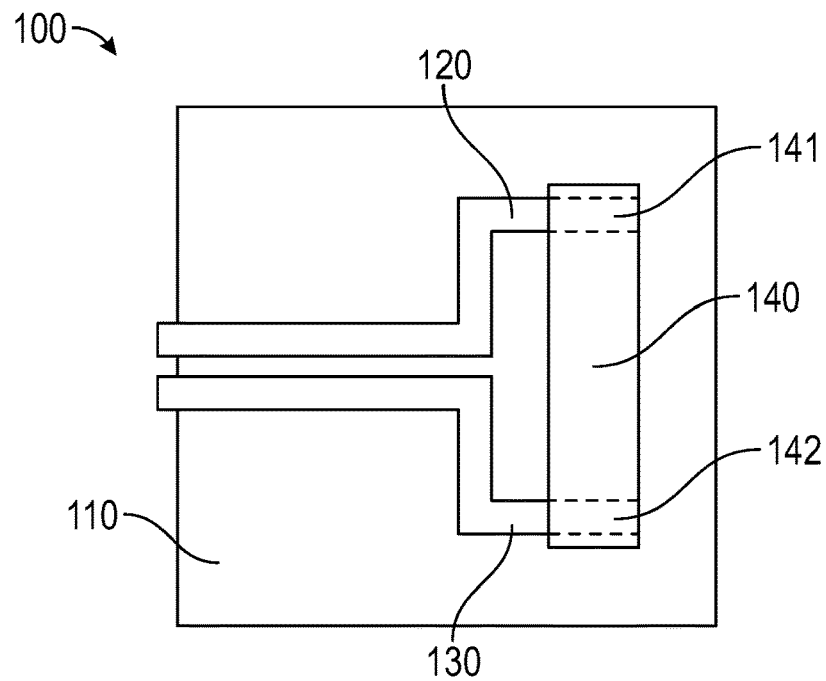
FIG. 1 depicts an embodiment of a sensor.

One embodiment of sensor is depicted at FIG. 1. The sensor 100 of FIG. 1 includes a substrate 110 onto which an electrode is disposed, wherein the electrode includes a first contact 120 and a second contact 130. The sensor also includes a buckypaper 140, which has a first portion 141 that contacts the first contact 120 of the electrode, and a second portion 142 that contacts the second contact 130 of the electrode.

In some embodiments, the sensors described herein are flexible sensors. Therefore, at least one component of the sensors may be flexible, such as the substrate, one or more electrodes, and one or more buckypapers.

In some embodiments, one electrode is disposed on the first surface of the substrate. In some embodiments, more than one electrode is disposed on the first surface of the substrate. For example, at least two electrodes, at least 10 electrodes, at least 50 electrodes, at least 100 electrodes, at least 1,000 electrodes, or more may be disposed on a first surface of a substrate. In some embodiments, 1 to 1,000, 1 to 500, 1 to 250, 1 to 100, 1 to 50, 1 to 25, or 1 to 10 electrodes are disposed on a first surface of a substrate. When more than one electrode is disposed on a surface of a substrate, the electrodes may be identical or different (e.g., different materials, different configurations, etc.). The electrodes may be arranged in any manner, e.g., a regular pattern, an irregular pattern, etc. Each electrode disposed on a first surface of a substrate may be in contact with one buckypaper, or, in some instances, more than one buckypaper.

In some embodiments, at least one electrode is disposed on a first surface of a substrate, and at least one electrode is disposed on a second surface of a substrate. For example, at least two electrodes, at least 10 electrodes, at least 50 electrodes, at least 100 electrodes, at least 1,000 electrodes, or more may be disposed on a first surface of a substrate, and at least two electrodes, at least 10 electrodes, at least 50 electrodes, at least 100 electrodes, at least 1,000 electrodes, or more may be disposed on a second surface of a substrate. In some embodiments, 1 to 1,000, 1 to 500, 1 to 250, 1 to 100, 1 to 50, 1 to 25, or 1 to 10 electrodes are disposed on each of a first surface of a substrate and a second surface of a substrate. When at least one electrode is disposed on a first surface and a second surface of a substrate, the electrodes may be identical or different (e.g., different materials, different configurations, etc.). The electrodes may be arranged in any manner, e.g., a regular pattern, an irregular pattern, etc. Each electrode disposed on a first surface or a second surface of a substrate may be in contact with one buckypaper, or, in some instances, more than one buckypaper.

The sensors provided herein include strain sensors. The strain sensors may be configured to detect any strain or range of strains. In some embodiments, the sensors are configured to detect strains of about 0.005% to about 0.025% within a 10 ms period. In some embodiments, the sensors are configured to detect strains of about 0.005% to about 0.02% within a 10 ms period. In some embodiments, the sensors are configured to detect strains of about 0.005% to about 0.015% within a 10 ms period. In some embodiments, the sensors are configured to detect strains of about 0.005% to about 0.01% within a 10 ms period.

The sensors provided herein, including strain sensors, may be configured to maintain a desirable gauge factor. In some embodiments, the sensor is configured to maintain substantially the same gauge factor for at least 10,000 cycles, at 1 Hz, of strain. In some embodiments, the sensor is configured to maintain substantially the same gauge factor for at least 9,000 cycles, at 1 Hz, of strain. In some embodiments, the sensor is configured to maintain substantially the same gauge factor for at least 8,000 cycles, at 1 Hz, of strain.

The sensors provided herein, including strain sensors, may be configured to have a desired piezoresistive response. In some embodiments, the sensor is configured to have a piezoresistive response that (i) is substantially null when the sensor is at rest, (ii) substantially linearly increases as a function of strain, or (iii) a combination thereof.

Substrates

The substrates of the sensors provided herein generally may include any material onto which an electrode may be disposed, by printing or otherwise. In some embodiments, the substrate of the sensors provided herein includes a polymer. As used herein, the term "polymer" includes a molecule that includes one or more monomers (i.e., repeat units), and includes oligomers, co-polymers, etc. A polymer of a substrate may be a linear polymer, branched polymer, comb polymer, star polymer, etc. In some embodiments, the substrate includes a woven or non-woven fabric. In some embodiments, the substrates include a woven or non-woven fabric and a polymer. The woven or non-woven fabric may be at least partially infiltrated with the polymer.

Non-limiting examples of polymers include polyvinyl alcohol, polyethylene terephthalate (PET), polyethylene oxide, or a combination thereof. Other polymers are envisioned. In some embodiments, the polymer is PET.

In some embodiments, the substrate is flexible. The flexibility of a substrate may be imparted by the material selected, the dimensions of the substrate (e.g., the thickness), or a combination thereof. As used herein, the phrase "flexible substrate" refers to a substrate that will bend without breaking, especially in response to one or more forces that may be applied to the device when in use (e.g., one or more forces applied by the typical movements of a human).

A substrate of the sensors provided herein generally may be of any size or shape. The size and/or shape of a substrate may, in some instances, be limited only by a method used to produce the sensors. In some embodiments, the substrate is a film. In some embodiments, the substrate is a film, and the first surface and the second surface of the substrate are the opposite sides of the film.

Electrodes

The electrodes provided herein generally include a first contact and a second contact. The first contact and the second contact generally may include any conductive material. The conductive material may include a metal, such as silver, gold, or a combination thereof. The conductive material may include carbon, such as $C_{60}$. The first contact and the second contact may include the same material or different materials.

The electrodes may be printed electrodes. A "printed electrode" is an electrode that is formed, at least in part, by disposing an ink on a substrate with a printer, such as an inkjet printer. The ink may be a water-based ink that includes conductive metal particles. In other words, the one or more printed electrodes may be formed from a water-based ink that includes conductive metal particles that is printed onto a substrate and then, optionally, dried. The drying may include active and/or passive drying. The ink, such as a water-based ink, may include a carbon electrode precursor, such as $C_{60}$.

In some embodiments, the metal particles are present in the water-based ink in an amount of about 10% to about 40%, by weight of the water-based ink. In some embodiments, the metal particles are present in the water-based ink in an amount of about 20% to about 30% by weight of the water-based ink. In some embodiments, the metal particles are present in the water-based ink in an amount of about 25% by weight of the water-based ink. The metal particles generally may include any metal that may serve as at least part of an electrode. In some embodiments, the metal particles include silver particles. In some embodiments, the metal particles include gold particles.

The first contact and the second contact of an electrode may have any shape or configuration. The shape and/or configuration of the first contact and the second contact may be the same or different. The first contact and the second contact may be arranged so that the first ends of the first contact and the second contact are configured to contact a first portion and the second portion, respectively, of a buckypaper. The second ends of the first contact and the second contact may be arranged so that the second ends are closer together than the first ends, which contact a buckypaper. The second ends of the first contact and the second contact may extend beyond the edge of a substrate, a laminating film, or both a substrate and a laminating film. Such a configuration may facilitate easier fabrication of a circuit and/or connection of the electrode to an instrument.

Laminating Films

The laminating films of the sensors provided herein generally may include any material that is compatible with the components of the sensors. In some embodiments, the laminating film is a material capable of protecting the sensor. For example, the laminating film may protect a sensor from damage that may occur during use and/or exposure to environmental elements, such as moisture.

A laminating film may cover all or a portion of the sensor. For example, a laminating film may cover all or a portion of a first surface of a substrate, and the electrodes and buckypapers of the first surface, all or a portion of a second surface of a substrate and the electrodes and buckypapers of the second surface, or a combination thereof. When a laminating film is disposed on one or both sides of a substrate, the laminating film may extend beyond the one or more edges of the substrate. The laminating film can include a polymeric material.

Buckypapers

The buckypapers of the sensors generally include networks of carbon nanomaterials. The carbon nanomaterials may include carbon nanofibers, carbon nanotubes, or a combination thereof. The carbon nanomaterials of a buckypaper may be randomly oriented, at least partially aligned, or a combination thereof. For example, a buckypaper may include a network of randomly oriented carbon nanomaterials, a network of substantially aligned carbon nanomaterials, or a network that includes a portion of randomly oriented carbon nanomaterials and a portion of substantially aligned carbon nanomaterials.

In some embodiments, the carbon nanomaterials include carbon nanotubes, such as multi-wall carbon nanotubes, single-wall carbon nanotubes, or a combination thereof. The carbon nanotubes may include pristine carbon nanotubes, functionalized carbon nanotubes, or a combination thereof.

In some embodiments, the carbon nanotubes have a thickness of about 4 µm to about 8 µm. In some embodiments, the carbon nanotubes have a thickness of about 6 µm.

In some embodiments, the carbon nanotubes have an electrical conductivity of about 180 S/cm to about 220 S/cm. In some embodiments, the carbon nanotubes have an electrical conductivity of about 200 S/cm.

In some embodiments, the carbon nanotubes have an elastic modulus of about 2.5 GPa to about 3.5 GPa. In some embodiments, the carbon nanotubes have an elastic modulus of about 3.0 GPa.

In some embodiments, the buckypapers of the sensors provided herein a thickness of about 0.003 mm to about 0.009 mm. In some embodiments, the buckypapers of the sensors provided herein a thickness of about 0.004 mm to about 0.008 mm. In some embodiments, the buckypapers of the sensors provided herein a thickness of about 0.006 mm.

The dimensions of the buckypapers used in the sensors provided herein are limited only by the size of a selected substrate and/or the desired number of buckypapers disposed on a substrate. In some embodiments, the buckypapers have a length of about 10 mm to about 30 mm, a width of about 1 mm to about 7 mm, and a thickness of about 0.003 mm to about 0.009 mm. In some embodiments, the buckypaper has a length of about 20 mm, a width of about 3 mm, and a thickness of about 0.006 mm. Generally, a buckypaper of any shape—e.g., square, rectangular (i.e., a strip of buckypaper), circular, etc.—may be used in the sensors provided herein.

Articles

Articles also are provided that include one or more of the sensors described herein. An article may include one sensor or two or more sensors.

The sensors may be affixed to the articles by any known means. For example, a sensor may be affixed to an article by an adhesive, one or more stitches, etc. As a further example, an article may include a compartment (e.g., a pocket) in which a sensor is at least partially disposed.

The articles provided herein may include wearable articles, such as clothing. The clothing articles may include shirts, pants, hats, gloves, coats, shoes, etc. The wearable articles may include accessories, such as watches, phones, health monitoring devices, motion detecting devices, etc. The articles provided herein may include medical devices, which, in some embodiments, are wearable medical devices.

Figure 6:
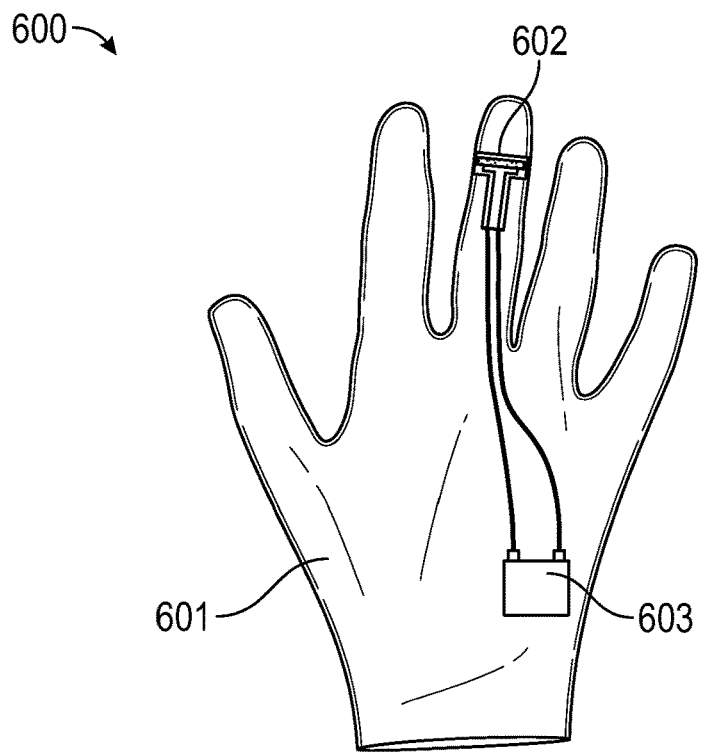
FIG. 6 depicts an embodiment of an article that includes a sensor.

An embodiment of an article is depicted at FIG. 6. The article 600 of FIG. 6 is a glove 601 that includes an embodiment of a sensor 602 provided herein. The sensor 602 is affixed to a finger portion of the glove 601 via an adhesive. The sensor 602 is connected to an instrument 603, which forms a circuit and facilitates collection of data.

When the articles include a fabric, the sensors may be attached to the fabric by sewing or otherwise. Fabrics having pockets to house the sensors also may be used to form the articles described herein.

Methods

Methods of forming sensors also are proved herein.

In some embodiments, the methods include providing an electrode disposed on a substrate. An electrode may be disposed on a substrate by any known means. For example, the providing of an electrode may include disposing (i) an ink that includes a liquid and conductive metal particles, or (ii) a molten metal on a substrate. The liquid of the ink may include water and/or an organic liquid. The disposing of an electrode on a substrate may include printing, such as with an inkjet printer, an ink on the substrate.

In some embodiments, the providing of an electrode disposed on a substrate includes printing with a printer, such as an inkjet printer, a water-based ink including conductive metal particles on a surface of the substrate to form the electrode. In some embodiments, one electrode is printed on a surface of the substrate. In some embodiments, at least one electrode is printed on a first surface of the substrate, and at least one electrode is printed on a second surface of the substrate. In some embodiments, more than one electrode is printed on a first surface and/or second surface of a substrate. When more than one electrode is printed on a first surface and/or second surface of a substrate, then the electrodes may be arranged in an array, as shown, for example, at FIG. 2A.

In some embodiments, metal particles are present in the water-based ink at an amount of about 10% to about 40% by weight, based on the weight of the water-based ink. In some embodiments, metal particles are present in the water-based ink at an amount of about 20% to about 30% by weight, based on the weight of the water-based ink. In some embodiments, metal particles are present in the water-based ink at an amount of about 25% by weight, based on the weight of the water-based ink. In some embodiments, the metal particles include silver particles, gold particles, or a combination thereof. In some embodiments, the printer is an ink jet printer. After printing, the water-based ink may be dried. The drying of the water-based ink may include active drying (e.g., with a fan, heat, etc.) and/or passing drying.

Figure 2A:
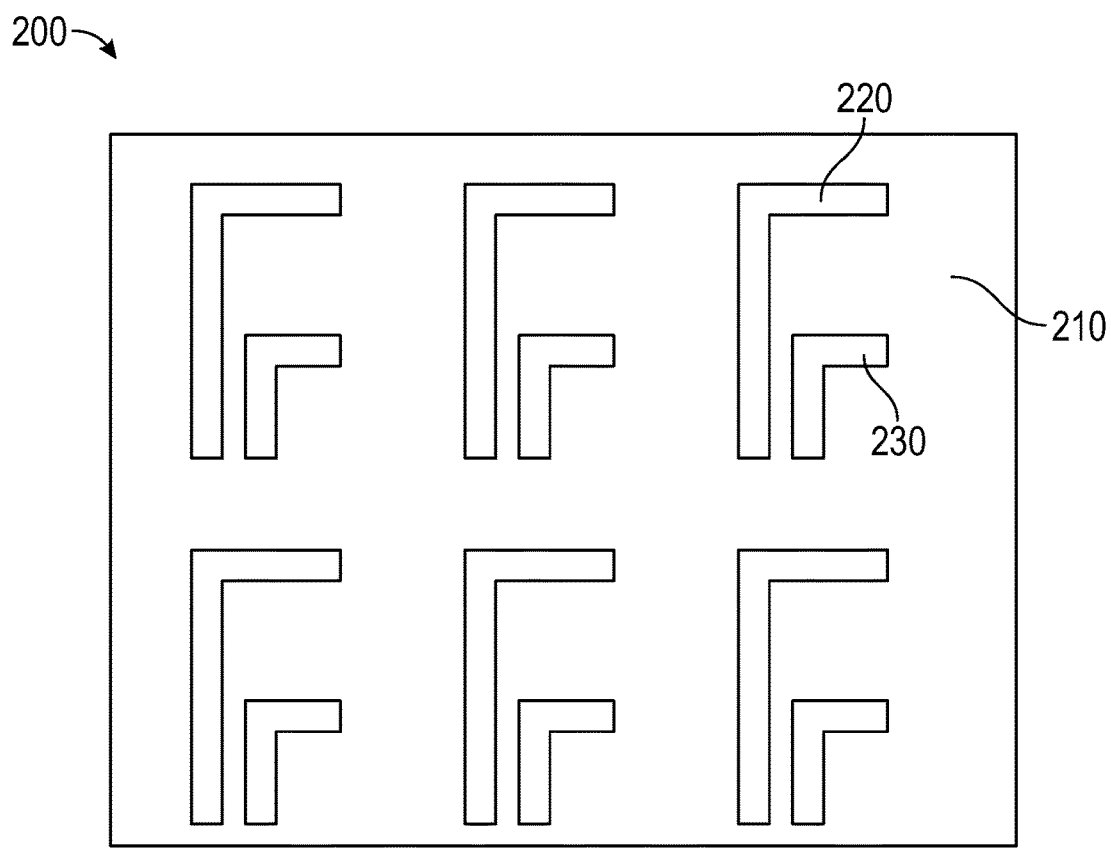
FIG. 2A depicts an embodiment of an array of electrodes.

FIG. 2A depicts an embodiment of an array of silver electrodes disposed on a substrate by inkjet printing. The material 200 of FIG. 2A includes a substrate 210 onto which an array of electrodes is disposed, wherein each electrode includes a first contact 220 and a second contact 230.

Figure 2B:
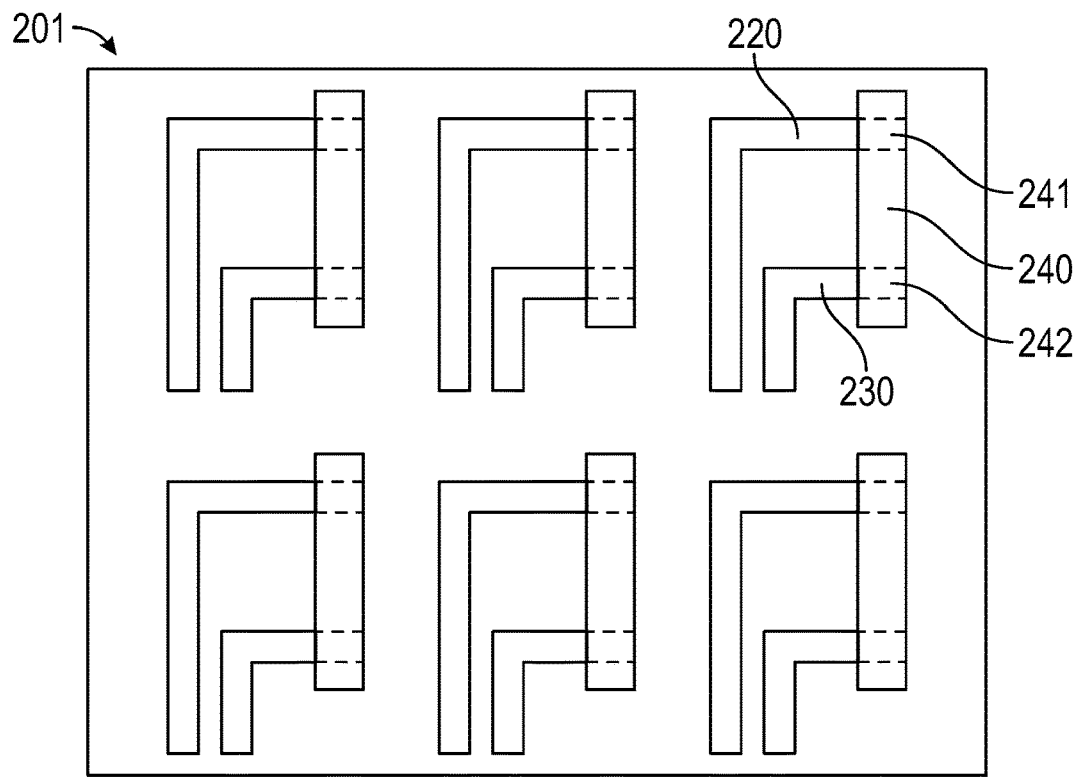
FIG. 2B depicts an embodiment of an array of electrodes and buckypapers.

In some embodiments, the methods described herein include providing a buckypaper having a first portion and a second portion; and arranging the buckypaper such that the first portion of the buckypaper contacts the first contact of the electrode, and the second portion of the buckypaper contacts the second contact of the electrode to form the sensor. The first portion of the buckypaper and the second portion of the buckypaper, in some embodiments, are portions at or near the ends of the buckypaper, including when the buckypaper has a rectangular shape, as depicted at FIG. 2B. The buckypapers may be affixed to the first contact and the second contact of the electrode by any known means, such as an adhesive, a laminating layer, etc. When a buckypaper is affixed to the first contact and a second contact of an electrode, a portion of the buckypaper may or may not contact the substrate. For example, in some embodiments, a buckypaper contacts a substrate at a region between the first contact and the second contact, and, in some embodiments, a buckypaper does not contact a substrate.

FIG. 2B depicts an embodiment of an array of sensors 201. The array of sensors 201 of FIG. 2B includes a buckypaper 240 that has a first portion 241 that contacts the first contact 220 of the electrode, and a second portion 242 that contacts the second contact 230 of the electrode.

In some embodiments, the methods provided herein include laminating at least a portion of a sensor. The laminating of at least a portion of a sensor may include any known technique that uses any known laminating materials.

In some embodiments, a laminating material is applied to a first surface of a substrate, a second surface of a substrate, or both a first surface and a second surface of a substrate. In some embodiments, a substrate includes an array of electrodes and buckypapers, and the array is divided into sections having one or more electrodes/buckypapers prior to lamination. In some embodiments, a substrate includes an array of electrodes and buckypapers, and the array is laminated prior to dividing the array into groups of one or more electrodes/buckypapers, as depicted at FIG. 2C.

Figure 2C:
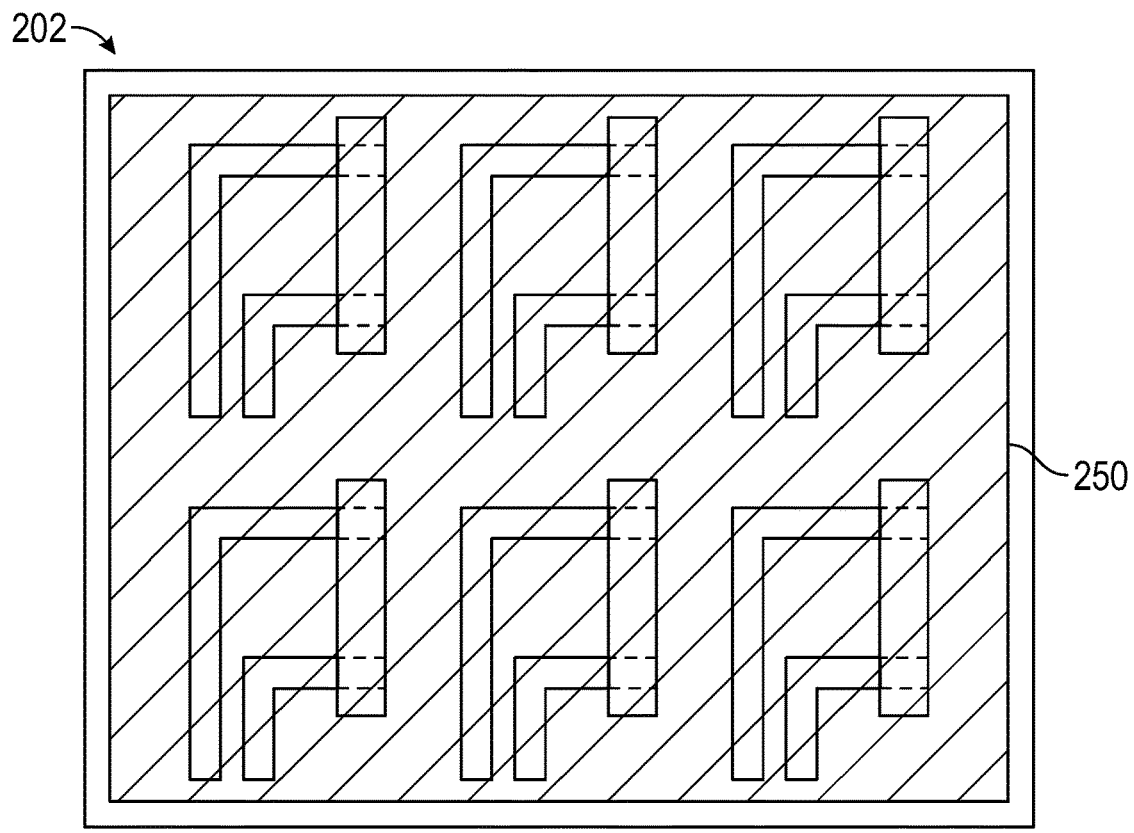
FIG. 2C depicts an embodiment of a laminated array of electrodes and buckypapers.

FIG. 2C depicts an embodiment of a laminated array of sensors 202. The laminated array of sensors 202 includes a laminating layer 250 disposed on the surface of the substrate that hosts the array of electrodes (220, 230) and buckypapers 240.

Figure 2D:
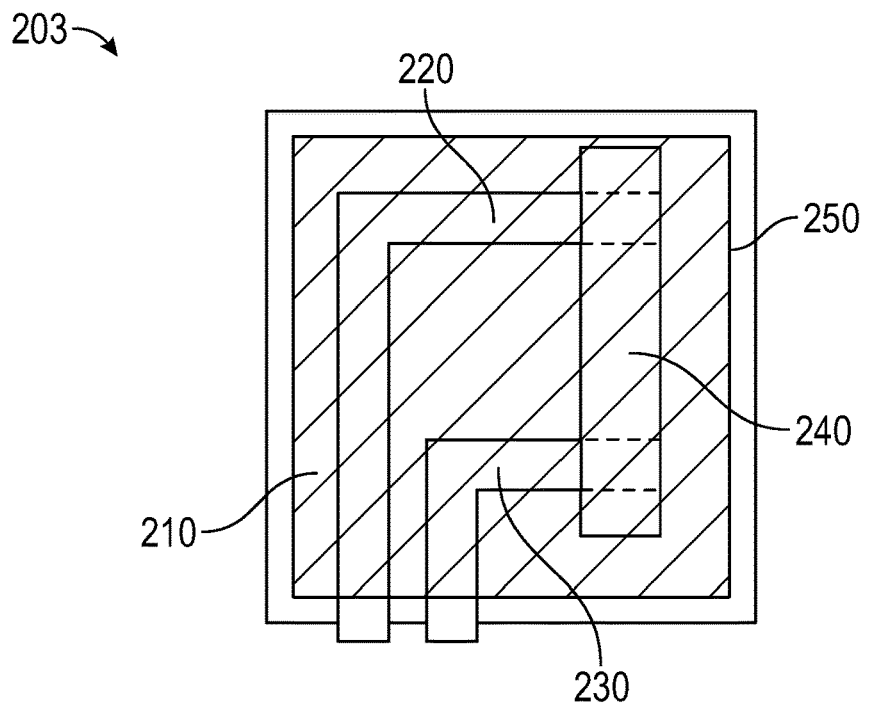
FIG. 2D depicts an embodiment of a laminated sensor that includes one electrode and one buckypaper.

FIG. 2D depicts an embodiment of a laminated sensor 203 obtained by dividing the substrate 210 of FIG. 2C into sections that include one electrode (220, 230) and one buckypaper 240 disposed on a portion of the substrate 210, and laminated with a portion of the laminating layer 250.

In some embodiments, the providing of a buckypaper includes providing a suspension that includes carbon nanotubes and a non-solvent liquid; and filtering the suspension to form the buckypaper. The method may also include drying the buckypaper, annealing the buckypaper, or a combination thereof. The formation of a suspension that includes carbon nanotubes and a non-solvent liquid and the filtering of the suspension may be achieved by any known technique, such as those described at U.S. Pat. No. 9,909,259 and U.S. Patent Application Publication No. 2011/0111279, which are incorporated herein by reference.

In some embodiments, the annealing of the buckypaper includes heating the buckypaper to a temperature of about 750° C. to about 900° C. for about 1 hours to about 7 hours. In some embodiments, the annealing of the buckypaper includes heating the buckypaper to a temperature of about 850° C. for about 4 hours.

In some embodiments, the carbon nanotubes are substantially uniformly dispersed in the suspension. A substantially uniform dispersion may be achieved using any known technique, such as stirring, sonication, etc. In some embodiments, the suspension includes a surfactant, such as TRITON®-X surfactant (HONEYWELL FLUKA™, USA). The surfactant may be present in a suspension at any concentration. In some embodiments, a surfactant is present in a suspension at a concentration about 0.001% to about 5% by weight, or about 0.001% to about 1% by weight, based on the weight of a suspension.

The terms "a," "an," and "the" are intended to include plural alternatives, e.g., at least one. For instance, the disclosure of "a substrate," "a buckypaper," and the like, is meant to encompass one, or mixtures or combinations of more than one substrate, buckypaper, and the like, unless otherwise specified.

In the descriptions provided herein, the terms "includes," "is," "containing," "having," and "comprises" are used in an open-ended fashion, and thus should be interpreted to mean "including, but not limited to." When methods or systems are claimed or described in terms of "comprising" various components or steps, the methods or systems can also "consist essentially of" or "consist of" the various components or steps, unless stated otherwise.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, that the carbon nanotubes have an elastic modulus of about 2.5 GPa to about 3.5 GPa. This range should be interpreted as encompassing values in a range of about 2.5 GPa to about 3.5 GPa, and further encompasses "about" each of 2.6 GPa, 2.7 GPa, 2.8 GPa, 2.9 GPa, 3.0 GPa, 3.1 GPa, 3.2 GPa, 3.3 GPa, and 3.4 GPa, including any ranges and sub-ranges between any of these values.

The processes described herein may be carried out or performed in any suitable order as desired in various implementations. Additionally, in certain implementations, at least a portion of the processes may be carried out in parallel. Furthermore, in certain implementations, less than or more than the processes described may be performed.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects will be apparent to those skilled in the art from consideration of the specification and practice of the invention disclosed herein.

Example 1—Multi-Wall Carbon Nanotube Buckypaper Fabrication

The fabrication process of this example for creating a carbon nanotube buckypaper (CNT-BP) included creating a uniform dispersion of CNTs via sonication.

Multi-wall CNTs (MWCNTs) were used in this example. The MWCNT-BPs produced in this example were 6 μm thick, exhibited an electrical conductivity of 200 S/cm, and had an elastic modulus of nearly 3 GPa.

The buckypaper fabrication procedure of this example was similar to procedures disclosed in the literature, however, TRITON®-X surfactant (HONEYWELL FLUKA™, USA) was added to the suspensions to improve the CNT dispersions by reducing the surface energies between CNT bundles.

The TRITON®-X surfactant (HONEYWELL FLUKA™, USA) was added to reduce or minimize the number of large CNT bundles in the dispersions. Highly dispersed CNTs were believed to facilitate higher quality buckypapers in terms of mechanical and/or electrical properties.

After dispersing the CNTs, the suspensions were then filtered onto a substrate through a mesh filter. After drying the remaining solvent, the resulting buckypapers were peeled from the substrate.

The films were repeatedly washed with distilled water, and annealed at 850° C. under argon gas for 4 hours to remove or reduce residual surfactant and/or impurities.

Several MWCNT-BPs also were produced in this example with the apparatus described at U.S. Pat. No. 9,909,259, which is incorporated herein by reference.

A buckypaper sample produced by the procedure of this example included a continuous roll of buckypaper having a length of about 2 meters. Scanning electron microscopy (SEM) images of this buckypaper sample were collected at 100× and 100,000× magnification.

The SEM images revealed that the buckypapers of this example included tightly packed CNT networks compared to solvent-casted CNT/polymer sensors, which include CNT networks infiltrated by an insulating matrix.

The dense, conductive network of the buckypapers made by the procedures of this example was advantageous, because the dense, conductive network likely provided the buckypapers with a more sensitive response to strain changes.

Example 2—Ink-Jet Printed Sensor

The sensor structure of this example included a strip of buckypaper (20 mm×3 mm×0.006 mm), a polyethylene terephthalate (PET) substrate with printed circuitry on its surface, and a laminated film to protect the sensor components and hold the BP strip in position.

The manufacturing process of this example included [1] printing silver electrodes on a polymer substrate with a commercially-available ink-jet printer, [2] positioning the strips of buckypaper on the electrodes, and [3] laminating the polymer substrate onto which the buckypaper strips had been positioned.

The manufacturing process of this example was low-cost and scalable due at least in part to the simplicity and commercial availability of the printing technology.

The silver ink electrodes were printed on a thin PET substrate using a low-cost, commercial one-pass printer (i.e., EPSON® STYLUS® inkjet printer).

A commercially available, water-based silver ink was used (METALON® conductive ink, NOVACENTRIX®, USA). The ink's composition included 25 wt. % silver particles (d 60-80 nm), 1-15 wt. % ethylene glycol, and 60-75 wt. % water.

The ink was emission-free and dried quickly, and the low-cost printer could print on a large-scale with minimal waste.

After the silver electrodes were printed, a buckypaper strip (2 cm×0.5 cm×7 μm) was positioned between the substrate's printed contacts and a laminating film, and then the substrate and buckypaper strips were laminated.

The buckypaper of this example was thin and avoided or minimized waviness in the final laminated structure.

The printed electrodes provided each end of the buckypaper strips with a fixed electrical contact. To facilitate the electrical contact with a circuit, the ends of the printed silver electrodes, which were closely-paired, were crimped with male connectors using a NICOMATIC® CRIMPFLEX® tool.

The PET substrate of this example was selected because its thinness imparted the resulting products with flexibility. Thicker substrates may be used, but bending strain generally decreases as thickness increases.

The buckypaper stripes of this example also had a desirable piezoresistivity response to stress. It was believed that the dense network of conductive CNTs promoted a seamless flow of current; however, under tensile stress, the network stretched and likely became less dense. This could have reduced the number of percolative pathways, which, in turn, could have reduced a buckypaper strip's conductivity. Therefore, the buckypaper strip's resistance could have changed as the CNT network deformed.

The reversible changes in the CNT networks of the buckypaper strips due to tensile and compression strains could impact the characteristics of the buckypaper strips.

As the buckypaper strip was stretched, the number of conductive paths reduced and there were fewer tunneling effects, which increased resistance (see, e.g., Wang, X. et al. Materials & Design, 2015, 88, 414-419; Gong, S. et al. Polymer, 2014, 55(16), 4136-4149; and Lee, B. M. et al. Journal of Materials Science, 2015, 50(7), 2973-2983). As the CNT network of the buckypaper strip was compressed, the opposite occurred (i.e., the number of conductive paths increased and there were more tunneling effects), which increased conductivity and reduced resistance (see, e.g., Kumar, V. et al. Carbon, 2016, 110, 62-68).

The manufacturing process of this example relied, in part, on inkjet printing (IJP), which imparted to the process a shorter production time, lower cost, high spatial resolution, and good reproducibility. The use of inkjet printing also minimized waste. Therefore, the use of inkjet printing permitted the use of functional inks and 3D substrates, which allowed for the rapid production of the devices of this example.

Example 3—Characterization

Strain gauge measurements were carried out using a DEWESOFT® SIRIUS® STG-Multi card. The printed sample was fastened to a flexible polyvinyl chloride (PVC) substrate (150 mm×25 mm×3 mm) using an epoxy-based adhesive. The PVC substrate was fixed to a linear actuator (NITEK® GDI 350ES500S), and the actuator applied periodic (1 Hz) strains of 0.4% with highly accurate positional control.

To better access the sensor's performance, a metallic, commercial strain gauge with a gauge factor of 2.5 was also fastened to the PVC substrate. Both strain gauges were connected to a Wheatstone bridge, and the measurements were recorded on a DEWESOFT® data acquisition card.

The buckypapers' electrical resistance included three components: (1) the intrinsic resistance ($R_{Individual}$) of the individual CNTs, (2) the contact resistance ($R_{Contact}$) between the CNTs, and (3) the tunneling resistance ($R_{Tunneling}$) between the CNTs.

However, $R_{Individual}$ played a negligible role in the buckypapers' piezoresistivity, due to their extraordinarily high elastic modulus, which indicated that a large amount of stress would be needed to strain the individual nanotubes.

The increasing number of gaps in the network caused an increase in electrical resistance by disconnecting percolation pathways. As presented at Equation 1, the total resistance of the CNT film was calculated as $R=R_{Individual}+R_{joint}$.

The $R_{joint}$ component could be further divided into the contact resistance $R_{Contact}$ for the CNTs in physical contact each other, and tunneling resistance $R_{Tunneling}$ for the CNTs separated by small gaps.

$$R_{BP} = R_{Individual} + \text{[illegible]} \tag{1}$$

The individual CNTs had an elastic modulus that approached 1 TPA; thus, 80 MPa of stress was required to produce micro-strains (0.01%) in a CNT. This high stiffness indicated that their contributions ($R_{Individual}$) to a buckypaper's piezoresistivity were negligible. The weak interactions at the nanotubes' joints influenced interfacial sliding, and dictated, at least in part, the buckypapers' piezoresistivity.

As nanotubes separated from each other, the network's electrical conductivity decreased. Therefore, it was deduced that $R_{Contact}$ and $R_{Tunneling}$ dictated the buckypapers' piezoresistivity.

Figure 3:
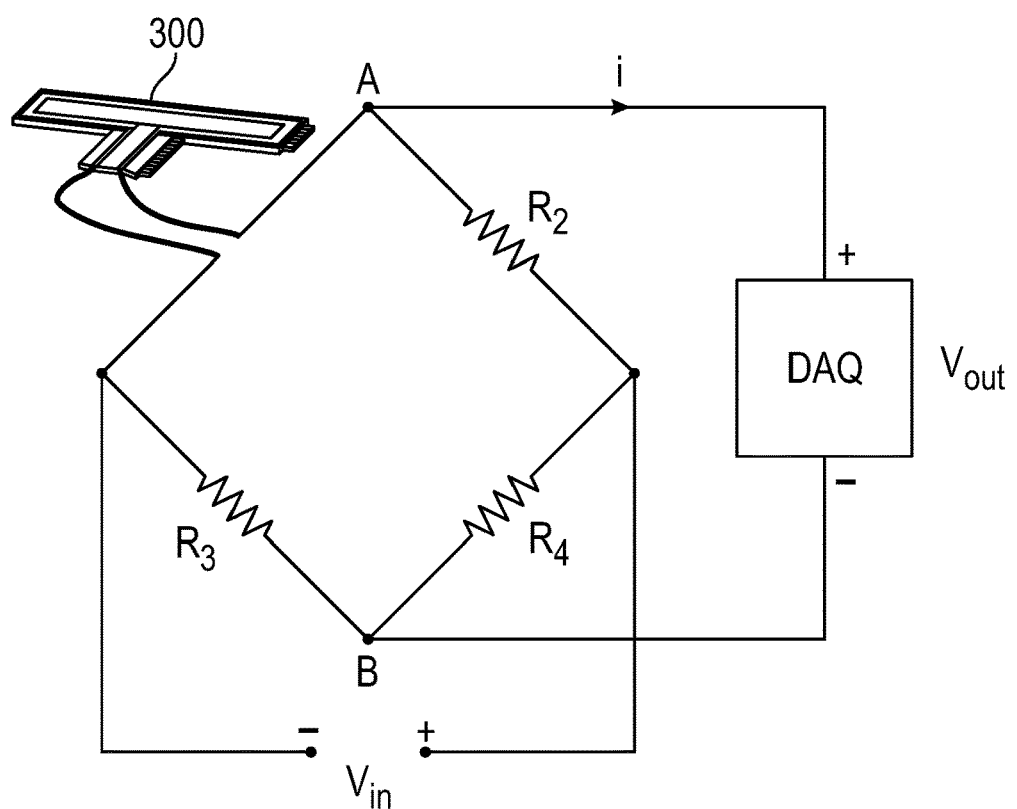
FIG. 3 depicts an embodiment of a Wheatstone bridge.

To determine the gauge factor, the buckypaper sensors were connected to a Wheatstone Quarter-Bridge circuit, as shown at FIG. 3. FIG. 3 is a schematic of the Wheatstone bridge characterization setup of this example, wherein $V_{in}=3V$, and $R_{BP}\approx R_2=R_3=R_4$ to balance the bridge. The schematic of FIG. 3 includes a buckypaper sensor 300.

A small voltage ($V_{in}=3V$) was applied to the circuit, and the voltage ($V_{out}$) across the buckypaper sensor was monitored. As presented at Equation 2, $V_{out}$ was expressed in terms of the circuit's resistors ($R_x$) and $V_{in}$.

$$V_{out} = V_A - V_B = \frac{R_{BP}R_4 - R_2R_3}{(R_{BP}+R_2)(R_3+R_4)}V_{in} \tag{2}$$

$R_{2-4}$ were known values that were chosen for the purpose of balancing the bridge. The bridge was balanced when $V_{out}$ was null when the sensor was at rest. Equation 3 is a general rule for balancing a Wheatstone bridge; thus, resistors equivalent to the sensor's resistance ($R_{BP}\approx 50\Omega$) were selected.

$$\frac{R_{BP}}{R_2} = \frac{R_3}{R_4} \quad (3)$$

Equation 4 expresses the change in the output voltage with respect to the change in buckypaper's resistance (ARBP) due to an applied strain.

$$\Delta V_{out} = \frac{[(R_{BP} + \Delta R_{BP})R_4 - R_2 R_3]}{[(R_{BP} + \Delta R_{BP}) + R_2](R_3 + R_4)} V_{in} - 0 \quad (4)$$

By using equivalent resistors for $R_{2-4}$, the three resistors were represented as a single resistance (R). Equation 4 was simplified to determine the sensor's sensitivity, as expressed at Equation 5.

$$\frac{\Delta V_{out}}{V_{in}} = \frac{\Delta R_{BP}}{4R} \quad (5)$$

By solving for $\Delta R_{BP}$, the gauge factor (GF) was determined using Equation 6. The gauge factor expressed the BP sensor's piezoresistive response was to strain $\left(\frac{\Delta l}{L}\right)$ $$GF = \frac{\frac{\Delta R_{BP}}{R_{BP}}}{\frac{\Delta l}{L}}$$

Figure 4A:
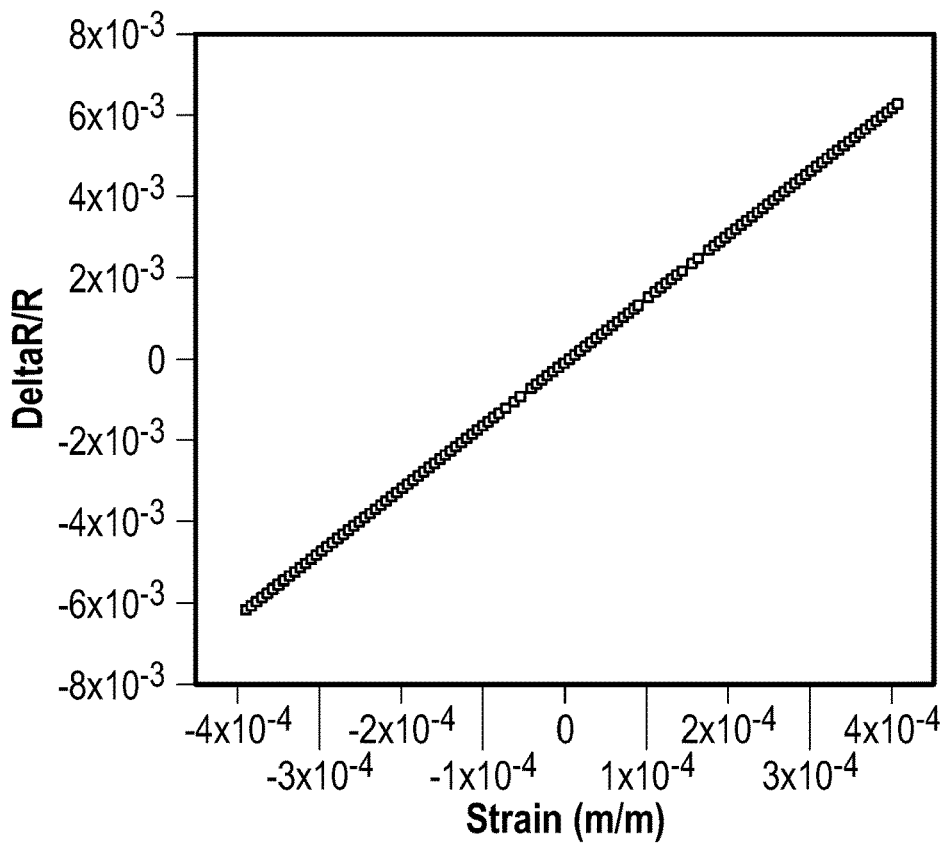
FIG. 4A and FIG. 4B depict the dynamic response of an embodiment of a sensor, including the measured sensitivity based on a Wheatstone bridge configuration (FIG. 4A), and a gauge factor versus strain comparison (FIG. 4B).
Figure 4B:
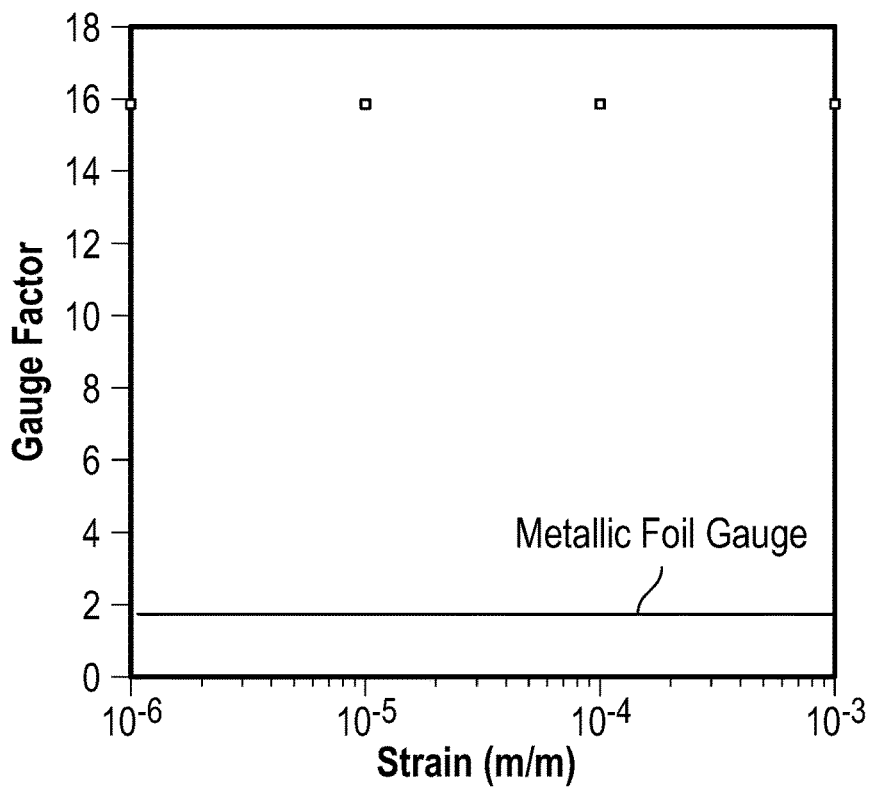

FIG. 4A and FIG. 4B depict the dynamic response of the sensor of Example 2, including the measured sensitivity based on the Wheatstone bridge configuration (FIG. 4A), and a gauge factor versus strain comparison (FIG. 4B).

FIG. 4A depicts the percent change in resistance as a function of strain, and the plot exhibits an excellent linear relationship. A strong, linear relationship with respect to both extension and compression mode resulted in a large strain window [−0.4%, 0.4%].

As expected, the BP sensor's piezoresistive response was null at rest, and linearly increased as a function of strain. The normalized resistance change reached (i) $6.23 \times 10^{-3}$ under 380 μm/m deformation in extension mode, and (ii) $6.22 \times 10^{-3}$ under 380 μm/m in compression mode. This reflected great symmetric behavior.

FIG. 4B displays a steady behavior at various levels of strain, as the gauge factor remained constant up to 0.1% strain.

In contrast, the metallic semiconductor gauge strain ranged up to 0.05%, and the gauge factor of the sensor of Example 2 was about eight times higher than the metallic gauge. The gauge factor of the CNT-BP sensor of Example 2 was low compared to the classical semiconductor sensor, which has a typical gauge factor between 50 and 100.

A comprehensive comparison of the CNT-BP sensor of Example 2 and recent CNT-based strain sensors was conducted. The recent CNT-based strain sensors that were a part of this analysis included those formed with (1) multi-wall CNTs and chewing gum, (2) a buckypaper of multi-wall CNTs and polyurethane, (3) a printed buckypaper and an epoxy resin, (4) a printed metallic sensor, and (5) a polymer nanocomposite containing multi-wall CNTs and single-wall CNTs (see, e.g., Rein, M. D. et al. Composites Science and Technology, 2011, 71(3), 373-381; Suzuki, K. K. et al. ACS Sensors, 2016, 1(6), 817-825; and Wang, X. et al. Materials & Design, 2015, 88, 414-419). Unlike the other tested sensors, the CNT-BP sensor of Example 2 maintained the same gauge factor for more than 10,000 cycles (at 1 Hz) of strain.

To test the buckypaper sensor's ability to detect subtle micro-strain, a series of the sensors of Example 2 were fastened to a latex glove using an adhesive. The sensors could detect strains as low as 0.005% within a 10 ms period. This can be important for motion sensing and structural health monitoring. This type of strain is virtually invisible and/or difficult to detect with current technology.

Figure 5:
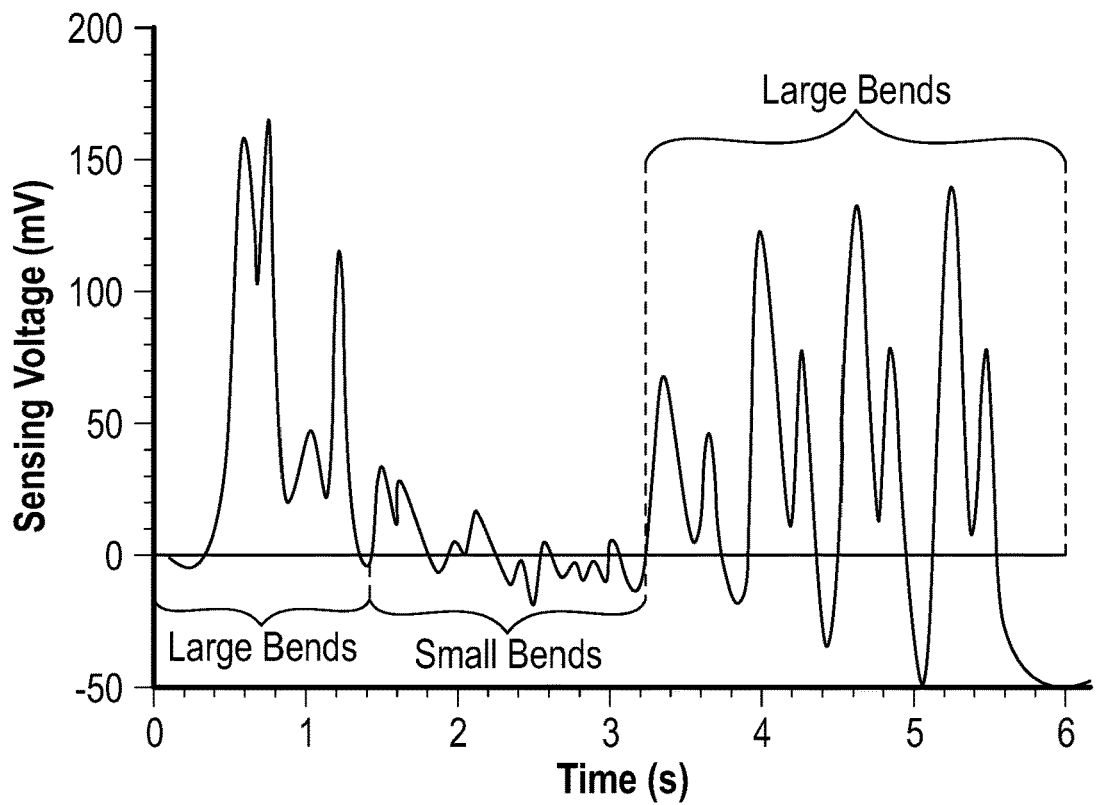
FIG. 5 depicts a plot of sensing voltage (mV) versus time for an embodiment of a sensor.

FIG. 5 depicts the experimental results obtained from monitoring the fingers of a user who worn a latex glove to which a sensor had been adhered. The sensor's output in response to obvious and subtle finger bending movements indicated that the BP sensor of Example 2 rapidly and consistently detected both forms of bending, and the responses were consistent.

The invention claimed is:

1. A sensor comprising:
a flexible substrate having a first surface and a second surface;
an electrode disposed on the first surface of the substrate, the electrode comprising a first contact and a second contact; and
a buckypaper having (i) a first portion that contacts the first contact of the electrode, and (ii) a second portion that contacts the second contact of the electrode;
wherein no other electrode physically contacts the buckypaper.

2. The sensor of claim 1, further comprising a laminating film disposed on at least a portion of (i) the first surface of the substrate, (ii) the second surface of the substrate, or (iii) both the first surface of the substrate and the second surface of the substrate.

3. The sensor of claim 1, wherein the buckypaper has a length of about 10 mm to about 30 mm, and a width of about 1 mm to about 7 mm.

4. The sensor of claim 1, wherein the buckypaper has a thickness of about 0.003 mm to about 0.009 mm.

5. The sensor of claim 1, wherein the buckypaper has a length of about 15 mm to about 25 mm, a width of about 3 mm to about 5 mm, and a thickness of about 0.004 mm to about 0.008 mm.

6. The sensor of claim 1, wherein the sensor is configured to detect strains of about 0.005% to about 0.025% within a 10 ms period.

7. The sensor of claim 1, wherein the sensor is configured to maintain substantially the same gauge factor for at least 10,000 cycles, at 1 Hz, of strain.

8. The sensor of claim 1, wherein sensor is configured to have a piezoresistive response that (i) is substantially null when the sensor is at rest, (ii) substantially linearly increases as a function of strain, or (iii) a combination thereof.

9. An article comprising the sensor of claim 1.

10. The article of claim 9, wherein the article is a wearable article.

11. The article of claim 10, wherein the wearable article comprises clothing.

12. A method of forming a sensor, the method comprising:
providing an electrode disposed on a substrate, wherein the electrode comprises a first contact and a second contact;
providing a buckypaper having a first portion and a second portion; and
arranging the buckypaper such that the first portion of the buckypaper contacts the first contact of the electrode, the second portion of the buckypaper contacts the second contact of the electrode to form the sensor, and the buckypaper does not physically contact any other electrode.

13. The method of claim 12, wherein the providing of the electrode comprises:
disposing an ink on the substrate to form the electrode, wherein the ink comprises (i) a liquid and conductive metal particles, or (ii) a molten metal.

14. The method of claim 13, wherein the conductive metal particles are present in the ink at an amount of about 10% to about 40% by weight, based on the weight of the ink.

15. The method of claim 13, wherein the disposing of the ink on the substrate comprises printing the ink on the substrate with a printer.

16. The method of claim 13, further comprising laminating at least a portion of the sensor.

17. The method of claim 13, wherein the providing of the buckypaper comprises:
providing a suspension comprising carbon nanomaterials and a non-solvent liquid; and
filtering the suspension to form the buckypaper.

18. The method of claim 17, wherein the method further comprises annealing the buckypaper.

19. The method of claim 17, wherein the carbon nanomaterials have a width of about 4 μm to about 8 μm and a thickness of about 6 μm.

20. The method of claim 17, wherein the carbon nanomaterials have an electrical conductivity of about 180 S/cm to about 220 S/cm.

21. The method of claim 17, wherein the carbon nanomaterials have an elastic modulus of about 2.5 GPa to about 3.5 GPa.

* * * * *